(12) United States Patent
Ash et al.

(10) Patent No.: US 8,132,104 B2
(45) Date of Patent: Mar. 6, 2012

(54) MULTI-MODAL ENTRY FOR ELECTRONIC CLINICAL DOCUMENTATION

(75) Inventors: Michael A. Ash, Parkville, MO (US);
John Q. Deverter, Liberty, MO (US);
Pramod Pagadala, Overland Park, KS (US)

(73) Assignee: Cerner Innovation, Inc., Overland Park, KS (US)

( * ) Notice: Subject to any disclaimer, the term of this patent is extended or adjusted under 35 U.S.C. 154(b) by 562 days.

(21) Appl. No.: 11/677,945

(22) Filed: Feb. 22, 2007

(65) Prior Publication Data
US 2008/0177537 A1 Jul. 24, 2008

Related U.S. Application Data

(60) Provisional application No. 60/886,448, filed on Jan. 24, 2007.

(51) Int. Cl.
*G06F 17/00* (2006.01)
*G06F 21/00* (2006.01)
(52) U.S. Cl. ........ 715/728; 715/209; 715/233; 715/802; 715/811; 704/270
(58) Field of Classification Search .......... 715/209–210, 715/221, 224, 233, 256, 704, 711, 716, 727–729, 715/789, 802, 809, 811, 816, 821; 704/235, 704/270, 275–276
See application file for complete search history.

(56) References Cited

U.S. PATENT DOCUMENTS

| | | | | |
|---|---|---|---|---|
| 6,834,264 B2* | 12/2004 | Lucas et al. | | 704/235 |
| 7,257,531 B2* | 8/2007 | Holub | | 704/235 |
| 7,516,070 B2* | 4/2009 | Kahn | | 704/235 |

OTHER PUBLICATIONS

Unknown Authors, "Embedding Sound Files into a PDF—playback and compatibility", Google Groups adobe.acrobat.macintosh Discussion Thread, Jun. 24-Aug. 11, 2004, http://groups.google.com/group/adobe.acrobat.macintosh/browse_thread/thread/58f6aeafc4e63157/74a332b798f024b0.*
Crocker, "Adding Voice Comments to your PDFs", http://replay.waybackmachine.org/20040810225530/http://www.planetpdf.com/enterprise/article.asp?ContentID=6062, Aug. 10, 2004.*

* cited by examiner

*Primary Examiner* — William Bashore
*Assistant Examiner* — Andrew Tank
(74) *Attorney, Agent, or Firm* — Shook, Hardy & Bacon L.L.P.

(57) ABSTRACT

Methods, computer-readable media, and systems for populating an electronic clinical document capable of receiving multiple types of data are provided. In one embodiment, dictation audio input is embedded directly into one or more sections of an electronic clinical document along with other data types, such as structured user input, free-text input, or system-generated input. An electronic clinical document having embedded dictation audio and other data types can receive transcribed text corresponding to the embedded dictation audio.

19 Claims, 11 Drawing Sheets

| FILE EDIT FORMAT TOOLS JOB MANAGEMENT AUDIO PLAYER HELP |
|---|

ASSIGNMENTS|DICTIONARY|TRANSCRIPTION DATA ENTRY|NORMALS|GENERAL/FORMAT ERROR

FACILITY INFORMATION
- FACILITY: MEDICAL CAMPUS WEST
- WORKTYPE +: CLINIC NOTE
- DICTATION SYSTEM JOB ID: 6759    LENGTH: 311000
- DATE / TIME: APR 18, 2003 12:21:05 PM
- DICTATING PHYSICIAN +: WILLIAM JERANEK

PATIENT INFORMATION
- LAST NAME: BLACK    FIRST: GERTRUDE    MI: NA
- MRN*: 1000115    LAST*: GYMNAST
- SSN: 555-66-7777    SEX: FEMALE    DOB: 12/28/1988
- LOOKUP PATIENT    CLEAR FIELDS    SEARCH FOR VISITS

VISIT INFORMATION
- ACCOUNT / VISIT*: 80194
- ADMISSION DATE: 04/26/2003    STATUS: OUTPATIENT
- DISCHARGE DATE: 04/26/2003
- SERVICE DATE: 04/26/2003    ENTER VISIT'S PHYSICIAN DATA

PHYSICIANS
- TYPE: ATTENDING    FULL NAME: ECRU, EVAN
- CO-SIGNER: TRANSOLUTIONS, USER
- CC: BLACK, BLANCHE
- MODIFY VISIT PHYSICIANS

PHYSICIAN CARBON COPY (CC) ADD AND CO-SIGNER SEARCH AREA
- LAST NAME*: B    FIRST NAME*:
- DICTATION ID*:    SEARCH CC
- CLEAR FIELDS    ADD ONE TIME

UPDATE INFORMATION AREA
PATIENT INFORMATION    ENTER PATIENT/VISIT DATA

LAST NAME: BLACK    MIDDLE NAME: NA    FIRST NAME: BLANCHE    PHYSICIAN NUMBER: 59342S    PHYSICIAN TYPE: CC

1002 →

A 6 YEAR OLD GIRL PRESENTS TO ENDOCRINE CLINIC FOR EVALUATION OF SHORT STATURE. PARENTS REPORT THAT SHE HAS ALWAYS BEEN THE SHORTEST GIRL IN HER CLASS, BUT THEY HAVE BECOME CONCERNED BECAUSE THE PATIENT'S 4 YEAR OLD SISTER IS NOW THE SAME HEIGHT AS SHE IS. THE PATIENT HAS NOT YET ATTAINED MENARCHE AND HER MOTHER REPORTS NO BREAST DEVELOPMENT. SHE HAS BEEN WELL WITH NO CHRONIC MEDICAL PROBLEMS, NO HOSPITALIZATIONS, AND NO SURGERIES. SHE LIVES WITH HER MOTHER, FATHER, AND SISTER AND SHE IS CURRENTLY A STRAIGHT A STUDENT IN THE SECOND GRADE. HER MOTHER IS 173 CM (5'8") AND WEIGHS 68 KG (150 POUNDS), SHE HAD MENARCHE AT AGE 12. THE PATIENT'S FATHER IS 185 CM (6'1") AND WEIGHS 95 KG (210 POUNDS), HE STARTED SHAVING AT AGE 15. THERE IS NO FAMILY HISTORY OF ANY MEDICAL PROBLEMS. THE PATIENT WAS 43 CM (17 INCHES) LONG AT TERM.

1004 →

\*\*\*\*\*\*\* PRELIMINARY REPORT \*\*\*\*\*\*\*

PATIENT: BARONIAN, ELLA    MRN: 00-00-0432
AGE: 6    GENDER: FEMALE    DOB: 07/07/1999
ASSOCIATED DIAGNOSIS:
AUTHOR: JONES, JOHN
SERVICE DATE: 2/14/2006

HISTORY OF PRESENT ILLNESS
ID - 817219

HEALTH STATUS
  ALLERGIES
    ALLERGY/REACTION PROFILE (ALL):
      ERTHROMYCIN
  CURRENT MEDICATION
    HOME MEDICATIONS
      FERROUS SULFATE (FER-IN-SOL 90MG/5ML ORAL SYRUP) 5ML PO ONCE DAILY #450ML 1 REFILL(S)

CONNECTION STATUS: CONNECTED    TRANSCRIPTIONIST STATUS: AVAILABLE    CURRENT JOB NUMBER: 162    NUMBER OF ASSIGNED JOBS: 1    TOTAL CHARACTER COUNT:    TOTAL LINE COUNT:

FIG. 11.

MULTI-MODAL ENTRY FOR ELECTRONIC CLINICAL DOCUMENTATION

CROSS-REFERENCE TO RELATED APPLICATIONS

This application claims the benefit of U.S. Provisional Application Ser. No. 60/886,448, filed Jan. 24, 2007, and entitled "Multi-Modal Entry For Electronic Clinical Documentation," which is hereby incorporated herein by reference.

STATEMENT REGARDING FEDERALLY SPONSORED RESEARCH OR DEVELOPMENT

Not applicable.

BACKGROUND OF THE INVENTION

In recent years, healthcare service providers have been making the transition from manual paper-based medical records to an electronic format. Commercially available computer software, such as PowerChart®, PowerChart Office®, and other Cerner Millennium® applications marketed by Cerner Corporation of Kansas City, Mo. have advanced the state of the art well beyond the conventional manual approach. Electronic-based records substantially increase the efficiency of healthcare providers and institutions. Electronic medical records also substantially reduce risks associated with high volumes of patient data and potential liabilities arising out of clerical errors or misinformation. The electronic format enhances communication between various providers and within institutions. As electronic clinical documentation continues to become increasingly prevalent, the variety of applications, electronic forms, electronic charts, and user interfaces, as well as the corresponding versatility of this format, continue to expand.

Dictation is commonly used by physicians and other healthcare providers to memorialize relevant information associated with patient interactions. For example, a physician may recite a summary of symptoms presented by a particular patient as well as the physician's probable diagnosis, intended plan of treatment, and any necessary follow-up steps. Dictation is often performed using tape recorders or other mechanical audio recording devices, and must be labeled and sent to a transcriptionist. Dictation cassettes can be mislabeled or lost, and are not an efficient means of preserving audio data that is to accompany medical records. Digital dictation devices are becoming more common, but even with this new medium, digital dictation files still must be imported, attached, or otherwise appended to existing records. Similar problems can arise with misidentification and mishandling of these unassociated electronic audio files within vast medical information systems.

In addition, many currently available forms of electronic clinical documentation are limited in their ability to combine multiple modes of data entry. For example, conventional electronic clinical forms do not allow a user to simultaneously import system-generated text, embed audio data, receive free-text, and receive structured input; nor do conventional forms allow a user to enter these multiple modes of data at multiple locations within an electronic clinical document. Some types of electronic medical documentation available today allow a user to merely attach an audio file to the documentation. This form of documentation is inadequate, however, as attachments to electronic medical records suffer from various problems. For example, transcriptionists tasked with transcribing the audio file generally do not have the benefit of seeing and understanding the context of the audio file within the electronic clinical document. As a result, the accuracy of the resulting transcription is mediocre, at best. Further, a physician or other provider who has recorded audio relevant to the documentation typically does not have access to the audio file once it is sent to be transcribed. As such, if the physician desires to review, edit or add to the dictated information, the physician must wait until the transcribed audio file is returned, which is inefficient and frustrating.

SUMMARY

Embodiments of the present invention relate to methods for populating an electronic clinical document. In one embodiment, an electronic clinical document capable of receiving multiple types of data, including dictation audio input, structured user input, free-text input, and system-generated input is provided. Into the electronic clinical document is subsequently received dictation audio input and at least one of structured user input, free-text input, and system-generated input. In one embodiment, the electronic clinical document includes a plurality of sections. Accordingly, the dictation audio input and the at least one of structured user input, free-text input, and system-generated input may be received into one of the plurality of sections. Additionally, if desired, the dictation audio input may be received into at least two of the plurality of sections.

Embodiments of the present invention also relate to one or more computer-readable media having computer-executable instructions embodied thereon for performing a method in a computerized healthcare system for populating an electronic clinical document having a plurality of sections. In one embodiment, the method includes providing an electronic clinical document having a plurality of sections, at least one of the plurality of sections being capable of receiving input of multiple data types, receiving dictation audio input into at least two of the plurality of sections, embedding the dictation audio input into each of the at least two sections, and presenting graphical representations indicative of the embedded dictation audio input in association with each of the at least two sections.

In other embodiments, the present invention relates to computer systems for presenting an electronic clinical document. In one embodiment, the system comprises a data store operative to store an electronic clinical document capable of receiving dictation audio input, structured user input, free-text input, and system-generated input, one or more receiving components operative to receive free-text input, structured user input, system-generated input, and dictation audio input, an embedding component operative to embed transcribed text associated with dictation audio input, and a user interface component operative to present a graphical representation of embedded dictation audio input relevant to a patient with whom the electronic clinical document is associated and to present at least one of free-text input, structured user input, and system-generated input on a common user interface.

BRIEF DESCRIPTION OF THE SEVERAL VIEWS OF THE DRAWINGS

The present invention is described in detail below with reference to the attached drawing figures, wherein:

FIG. 6 is an exemplary screen display of an electronic clinical document having a pop-up window indicative of an associated recording component, in accordance with an embodiment of the present invention;

FIG. 7 is an exemplary screen display of an electronic clinical document with a graphical representation indicative of embedded dictation audio input, in accordance with an embodiment of the present invention;

FIG. 8 is an exemplary screen display of an electronic clinical document with a transcription input window for receiving transcribed text associated with dictation audio input, in accordance with an embodiment of the present invention;

FIG. 9 is an exemplary screen display of an electronic clinical document showing transcribed text associated with dictation audio input that has been entered into a section of the document into which the dictation audio input was embedded, in accordance with an embodiment of the present invention;

FIG. 10 is an exemplary screen display for receiving transcribed text associated with dictation audio input into an electronic clinical document, in accordance with an embodiment of the present invention; and FIG. 11 is an exemplary screen display of an electronic clinical document showing multiple instances of embedded dictation audio input, in accordance with an embodiment of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention provide computerized methods, computer-readable media, and systems for populating and presenting an electronic clinical document capable of receiving multiple types of input, including dictation audio input, structured user input, free-text input, and system-generated input. An exemplary operating environment is described below, though one of ordinary skill in the art will appreciate that other suitable operating environments may be used.

Figure 1:
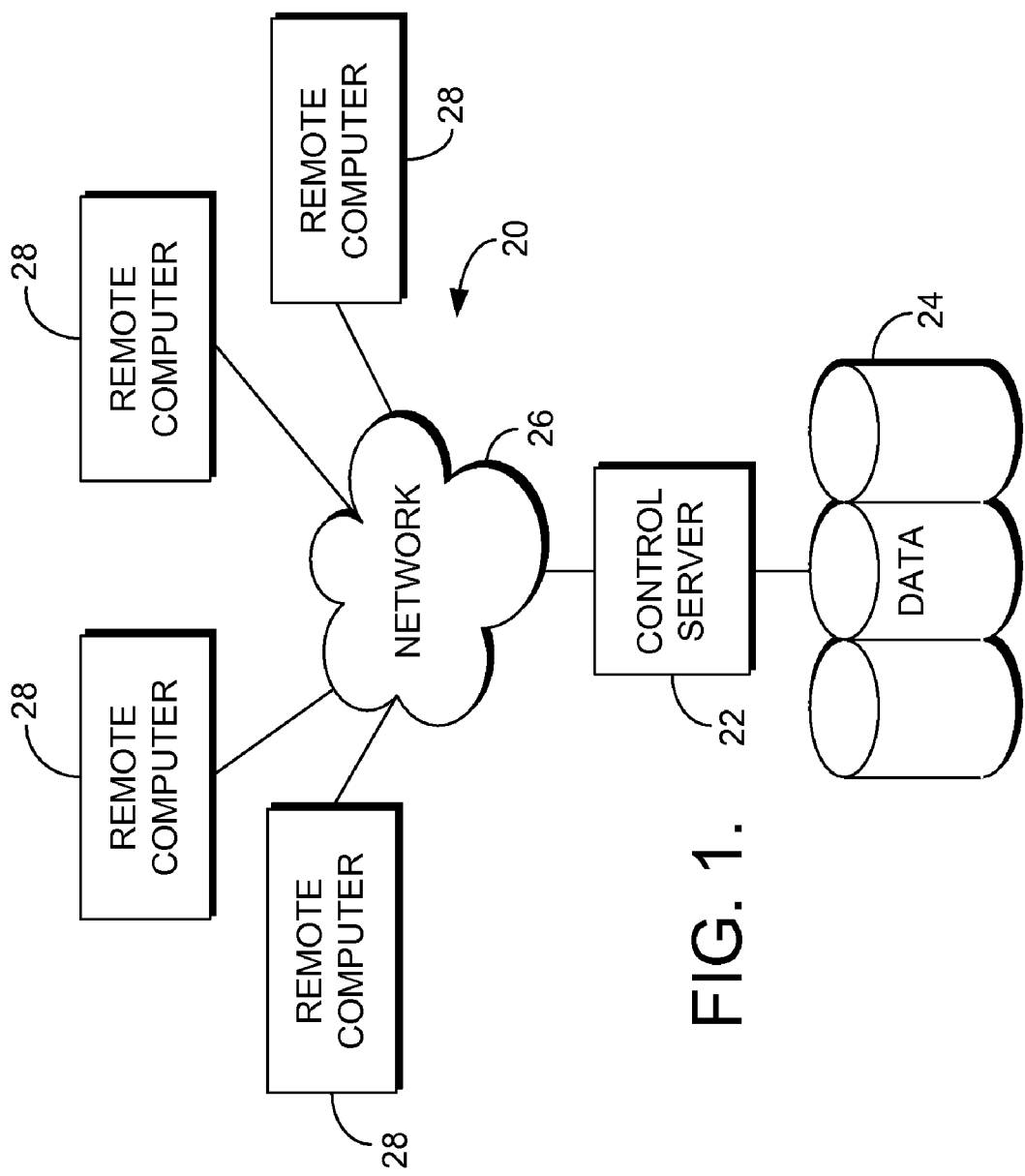
FIG. 1 is a block diagram of an exemplary computing system suitable for use in implementing embodiments of the present invention.

Referring to the drawings in general, and initially to FIG. 1 in particular, an exemplary computing system environment, for instance, a medical information computing system, on which the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a control server 22. Components of the control server 22 may include, without limitation, a processing unit, internal system memory, and a suitable system bus for coupling various system components, including database cluster 24, with the control server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 22 typically includes therein, or has access to, a variety of computer readable media, for instance, database cluster 24. Computer readable media can be any available media that may be accessed by control server 22, and includes volatile and nonvolatile media, as well as removable and nonremovable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage or other magnetic storage device, or any other medium which can be used to store the desired information and which may be accessed by control server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for control server 22. For example, the database cluster 24 can contain electronic clinical documents capable of receiving multiple types of input, including dictation audio input, structured user input, free-text input, and system-generated input. Database cluster 24 can contain electronic medical records for various patients. Data from these records can be used by the system to generate system-generated input to be populated into sections of electronic clinical documents. For example, a patient's vital signs or portions of a patient's medical history, which may have been recorded or stored elsewhere in the system, may be populated by the system into an electronic note documenting a particular patient encounter. Further, forms for supporting structured user input may also be stored in database cluster 24, and may be customized by a particular health care provider or institution. And, electronic clinical documents that have been populated with various forms of input can be stored in database cluster 24.

The control server 22 may operate in a computer network 26 using logical connections to one or more remote computers 28. Remote computers 28 may be located at a variety of locations in a medical environment, for example, but not limited to, clinical laboratories, hospitals and other inpatient settings, ambulatory settings, medical billing and financial offices, hospital administration settings, home health care environments, and clinicians' offices. Clinicians may include, but are not limited to, a treating physician or physicians, specialists such as surgeons, radiologists and cardiologists, emergency medical technicians, physicians' assistants, nurse practitioners, nurses, nurses' aides, pharmacists, dieticians, microbiologists, and the like. Remote computers 28 may also be physically located in non-traditional medical care environments so that the entire health care community may be capable of integration on the network. Remote computers 28 may be personal computers, servers, routers, network PCs, peer devices, other common network nodes, or the like, and may include some or all of the elements described above in relation to the control server 22.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the control server 22 may include a modem or other means for establishing communications over the WAN, such as the Internet. In a networked environment, program modules or portions thereof may be stored in the control server 22, in the database cluster 24, or on any of the remote computers 28. For example, and not by way of limitation, various application programs may reside on the memory associated with any one or all of the remote computers 28. Computer network 26 can be coupled to a remote computer 28 for purposes of allowing a transcriptionist to access electronic clinical documents stored on database cluster 24. It will be appreciated by those of ordinary skill in the art that the network connections shown are exemplary and other means of establishing a communications link between the computers (e.g., control server 22 and remote computers 28) may be utilized.

In operation, a user may enter commands and information into the control server 22 or convey the commands and information to the control server 22 via one or more of the remote computers 28 through input devices, such as a keyboard, a pointing device (commonly referred to as a mouse), a trackball, or a touch pad. For example, a keyboard and mouse can be used to input free-text data, structured form data, or to input user-driven-populated data (e.g., such as by selecting categories of data to be populated by the system) to be received by the control server 22 or by one or more of the remote computers 28. Other input devices may include, without limitation, microphones, satellite dishes, scanners, or the like.

Any type of microphone or other device capable of receiving audio input may be used to receive dictation audio input to be embedded into electronic clinical documents. Additionally, dictation audio input may be received by an external audio recording source and then imported into a remote computer 28 or into the control server 22. For example, a physician or other health care provider can dictate using a digital dictation device and then import the audio into a remote computer 28 or the control server 22. The imported dictation audio input can then be embedded into an electronic clinical document, as more fully described below.

The control server 22 and/or remote computers 28 can be coupled to a computer monitor or other graphical display device capable of conveying a user interface, such as the exemplary user interfaces discussed below with reference to FIGS. 4-11. The user interface can display free text, structured form data, system-generated data (including auto-populated data and user-driven populated data), as well as other graphical-based representations of data. The control server 22 and/or remote computers 28 may include other peripheral output devices, such as speakers and a printer. Speakers, for example, can allow a health care provider, transcriptionist, or other appropriate individual to play back dictation audio input that has been embedded into an electronic clinical document.

Although many other internal components of the control server 22 and the remote computers 28 are not shown, those of ordinary skill in the art will appreciate that such components and their interconnection are well known. Accordingly, additional details concerning the internal construction of the control server 22 and the remote computers 28 are not further disclosed herein.

Although methods and systems of embodiments of the present invention are described as being implemented in a WINDOWS operating system, operating in conjunction with an Internet-based system, one of ordinary skill in the art will recognize that the described methods and systems can be implemented in any system supporting the receipt and processing of healthcare orders and related information. As contemplated by the language above, the methods and systems of embodiments of the present invention may also be implemented on a stand-alone desktop, personal computer, or any other computing device used in a healthcare environment or any of a number of other locations.

As mentioned above, embodiments of the present invention provide computerized methods, computer-readable media, and systems for populating and presenting an electronic clinical document capable of receiving multiple types of input, including dictation audio input, structured user input, free-text input, and system-generated input. For simplicity, the particular user will often be referred to as a clinician. However, it will be understood that the particular user may be any healthcare professional, physician, or other provider, as described above.

Figure 2:
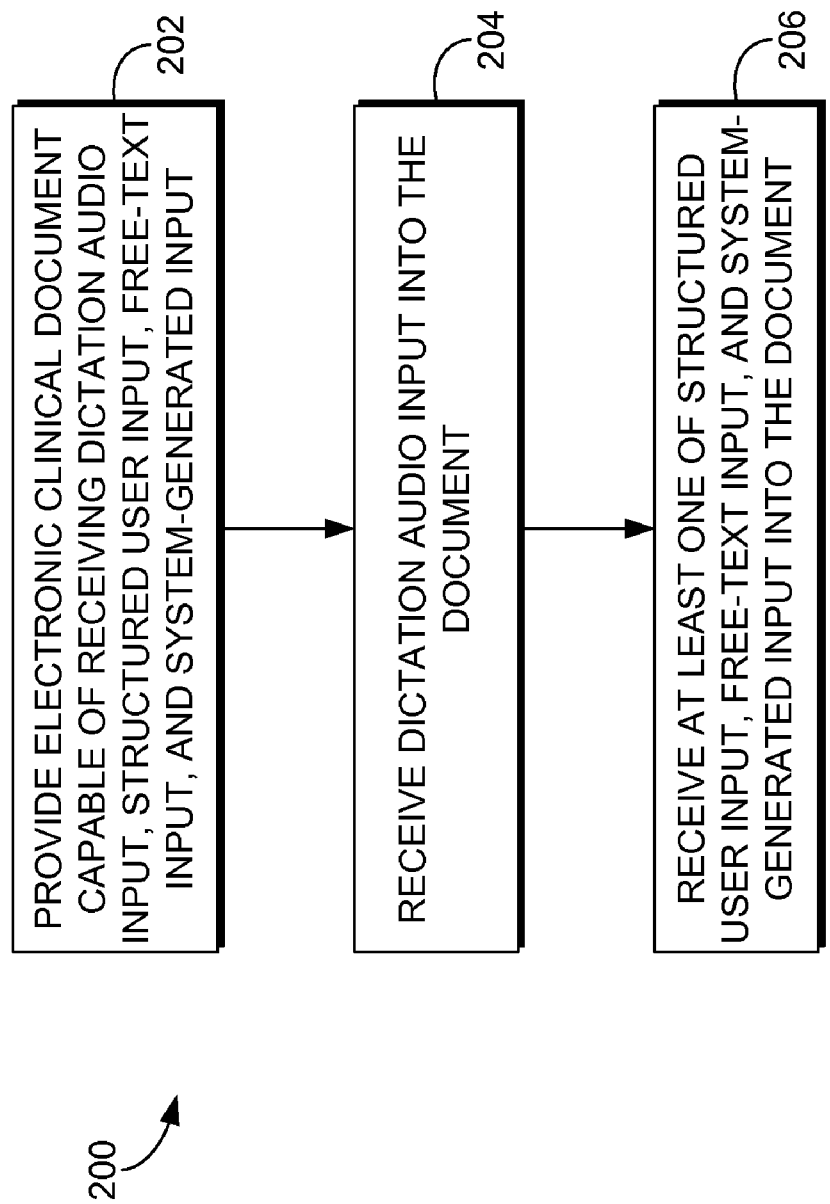
FIG. 2 is a flow diagram showing an exemplary method for populating an electronic clinical document with multiple types of data, in accordance with an embodiment of the present invention.

With reference to FIG. 2, an exemplary flow diagram representative of a method for populating an electronic clinical document using multiple types of data entry in accordance with an embodiment of the present invention is shown and referenced generally by reference numeral 200. Method 200 may be implemented using the above-described exemplary computing system environment (FIG. 1) and, by way of example only, may be utilized by a clinician to populate an electronic clinical document (e.g., an electronic medical record) associated with a patient. (The terms "individual", "person", and "patient" are used interchangeably herein and are not meant to limit the nature of the referenced individual in any way. Rather, the methods and systems described herein are equally applicable in, for instance, a veterinary setting. Further, use herein of the term "patient" is not meant to imply any particular relationship between the individual in question and those populating an electronic clinical document associated with the individual.)

Initially, as shown at block 202, an electronic clinical document capable of receiving data entry through a plurality of modes, including, but not limited to, dictation audio input, structured user input, free-text input, and system-generated input is provided. The electronic clinical document can be provided via any type of graphical display, such as a computer monitor or any other type of graphical presentation apparatus, such as for example, an LCD screen, a laptop display, or a handheld PDA device. An electronic clinical document can be any type of electronic medical documentation relevant to a particular patient and can be part of an electronic healthcare information technology system. An electronic clinical document can also be a clinical event document relating to a particular clinical event for a patient, including, by way of example only, a patient visit or encounter. By way of example and not limitation, electronic clinical documents may be clinical notes, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information. Electronic clinical documents may be stored within an overall electronic medical chart or electronic medical record associated with a patient.

The format for electronic clinical documents may be customized by the user and/or may be established by a particular healthcare institution, such as by using a profile stored in a database, such as database cluster 24, or by using a locally stored profile on a remote computer (e.g., remote computer 28 of FIG. 1).

"Dictation audio input", as the term is utilized herein, refers to audio data (for example, voice data recorded from a person's audible voice) that is recorded for the purpose of creating an audio record of information that is to be later transcribed or automatically converted into text and associated with the electronic clinical document. Clinicians, for example, frequently dictate notes and other reports to memorialize patient visits, diagnoses, and intended treatment plans. Dictation is used as a way to quickly capture the clinician's observations and recommendations in a format that can later be converted to text and entered into pertinent sections of electronic medical records for particular patients. In embodiments of the present invention, dictation audio input is stored in an electronic format. Any electronic audio format can be used, including, by way of example and not limitation, WAV files, MP3 files, and the like. Compressed or uncompressed formats can be used and are contemplated as being within the scope of embodiments of the present invention. In embodiments, dictation audio input can be recorded in real time by a clinician user, such as by using a PC microphone on a personal computer, and then embedded directly into an electronic clinical document. In other embodiments, dictation audio input can be stored in an electronic file, transferred to or imported into a system, and then embedded into an electronic clinical document. Any and all such variations and combinations thereof, are contemplated to be within the scope of embodiments hereof.

The electronic clinical document is also capable of receiving structured user input. For example, a clinical form or table which provides pre-defined structure designed for receiving user input relevant to particular aspects of a patient's condition and/or treatment may be used in accordance with embodiments of the present invention. The particular structure used to guide the user's input may be customized by a user according to the user's particular preferences (including particular fields frequently used by the user) or according to a profile established, e.g., by a particular healthcare institution and implemented across an electronic medical record system. For example, a clinician may wish to have a form designed to capture user input regarding a patient's ambulation during a patient visit. In this example, the clinician can select from a number of pre-defined options commonly used to describe and categorize issues and observations associated with the patient's appearance and movement. Any type of specific selection method can be used within the form designed for receiving structured user input. For example, boxes with check marks, circles, graphical highlights, or other graphical indicators may be used to visibly represent selections made within a particular clinical form or table.

Selections may be made using any input means, such as those described above in connection with the exemplary computing system of FIG. 1, including, for example, a keyboard, mouse, touch screen, touchpad, or other pointing device. In one embodiment, a single "click" with a mouse over a particular word or phrase, such as "with crutches", receives a positive input ("yes") associated with the field ("with crutches") and generates a graphical circle around the field. In this instance, the user has indicated that the patient was using crutches when the user met with the patient. In this embodiment, a second click with the mouse clears the selection and removes the graphical circle. In other embodiments, where appropriate, a negative input may be received with an additional mouse click. Though ambulation is provided as one example of a subject for which structured user input may be received, any type of clinical information relevant to the patient may be received via structured user input provided that a particular form or table having pre-defined selection parameters exists that is capable of capturing the information.

The electronic clinical document is further capable of receiving free-text input. Free-text input can be received by a user utilizing a keyboard, for example, to enter textual characters into a text field, box, region, or other section within the electronic clinical document. Free-text input is not constrained in the way that structured user input is constrained by pre-defined selection parameters. Any alpha-numeric characters or symbols may be entered as free-text. Free-text input may also be imported into the clinical document, such as by being "copied and pasted" from an e-mail or word processing document. Free-text input may be entered using any text-entry method, such as that used by common word-processing software. Free-text input may be used by a user to enter a brief summary of a patient visit or to enter a brief synopsis of a patient's medical history, for example. Any type of clinical information relevant to the patient may be entered into any section of the electronic clinical document using free-text input.

The electronic clinical document is further capable of receiving system-generated input. System-generated input may be data that is auto-populated by the computer system automatically retrieving information relevant to the patient that is available from other portions of the patient's electronic medical record, from other locations within the system, or from associated systems. For example, a particular user's or institution's profile may indicate that all patient identification information, vital signs, and all current medications prescribed to the patient that are stored in the system are to be populated into each clinical document that is generated whenever a particular user chooses to create a new electronic clinical document for the patient. Auto-population saves the user time by obviating the need to manually enter data into the electronic clinical document when the information is already available.

System-generated input may also be input using user-driven population, i.e. when, upon a request from the user, data that already exists for the patient is retrieved from other portions of the patient's record, from other locations within the system, or from associated systems, and input into a particular section or sections of the electronic clinical document. For example, user-driven-populated data may be input upon a user requesting that the patient's vital signs or current medications be populated into the particular electronic clinical document. In this case, the relevant data already exists within the patient's record, within the system, or within an associated system. The data is merely retrieved from the other location and used to populate a particular section or sections of the current electronic clinical document being generated. This differs from auto-population in that the data is not automatically populated into the document as a matter of course, but rather the user must request that the particular type of information be populated into the document. In embodiments of the present invention, either auto-populated data entry or user-driven-populated data entry, or any combination thereof, may be used as system-generated input.

Once the electronic clinical document capable of receiving the multiple modes of data entry has been provided, such as by way of a graphical user interface, multiple types of data input may be received. In the illustrated embodiment, dictation audio input is received into the electronic clinical document, as indicated at block 204, in addition to at least one of structured user input, free-text input, and system-generated input, as indicated at block 206. Any appropriate audio capture method can be used to capture the dictation audio input, such as an audio input device that is a part of the exemplary computing system environment described above with reference to FIG. 1. For example, a computer microphone (external or internal) may be used to capture the dictation audio spoken by a particular user. A graphical interface, which is more fully described below with reference to FIG. 6, can be used, for example, to allow the user to control the start and stop of the recording process. If a user is not satisfied with the particular recording, the audio file can be deleted and re-recorded by the user. Once the user is satisfied with the particular recording, the user can choose to save the dictation audio input, which is then embedded directly into the electronic clinical document at the location where the user selected to enter dictation audio input. A graphical representation, such as an icon, may be generated by the system and displayed at the particular location where the dictation audio input was embedded. In embodiments, a dictation audio identifier is assigned to the particular dictation audio input to identify it within the system, and that can be used by a pointer to serve as a reference between the dictation audio input and the document. The identifier associates the recorded dictation audio input with the particular patient, the particular electronic clinical document, and the particular location within the document. In one embodiment, the identifier is a multi-digit numeral.

In addition to real-time audio capture, previously recorded audio files can be embedded into sections of the electronic clinical document. In embodiments of the present invention, multiple dictation audio inputs can be received at multiple locations within an electronic clinical document, within a particular section of an electronic clinical document, and can be moved and/or copied from one location to another.

Receipt of at least one of structured user input, free-text input, and system-generated input may be into the same section or sections as the dictation audio input received at step 204, or can be received into a different section of the electronic clinical document. Any section of the electronic clinical document can optionally receive any of the types of input described, including dictation audio input, structured user input, free-text input, and system-generated input. For example, in a physical examination section of a clinical note being populated by a clinician for a patient, the clinician-user can enter dictation audio input, free-text input, structured user input, and system generated input. Each section has the ability to receive multiple types of data entry. Also, any order of data entry is possible using embodiments of the present invention. Additionally, auto-populated system-generated input may be entered automatically into the electronic clinical document when the document is initially created or accessed by the user. Further, an electronic clinical document can receive data input, be stored in the system for later access or editing, and additional input (including input from any of the above-described modes of data entry) can be entered into the electronic clinical document.

Figure 3:
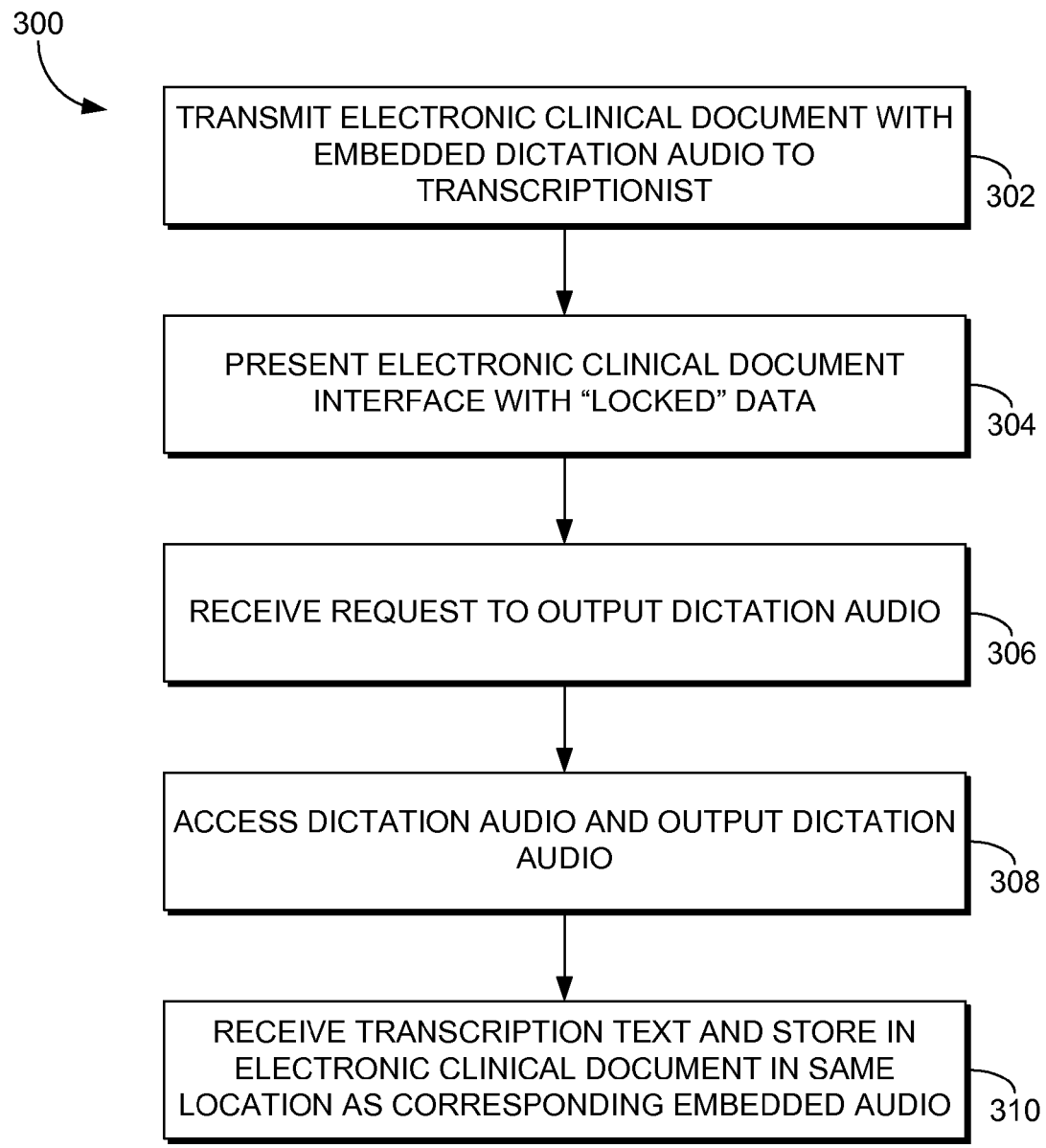
FIG. 3 is a flow diagram showing an exemplary method for receiving transcribed text into an electronic clinical document having embedded dictation audio input associated therewith, in accordance with an embodiment of the present invention.

With reference to FIG. 3, a detailed method 300 for receiving transcribed text associated with dictation audio input into an electronic clinical document having the dictation audio input embedded therein is represented by a flow diagram. After dictation audio input has been received into an electronic clinical document and embedded into one or more sections of the document, the dictation audio input may be transcribed. The electronic clinical document may have received none, any, or all of the other types of data entry described above in connection with FIG. 2, in addition to the dictation audio input. Initially, as indicated at block 302, the electronic clinical document having the embedded dictation audio is transmitted to a transcriptionist. The electronic clinical document may be transmitted in any format. The electronic clinical document may be itself sent to the transcriptionist or an electronic reference or link to the document may be sent. For example, an e-mail to a transcriptionist may be generated and sent once a clinician indicates that the document has dictation audio input that is ready to be transcribed. In the alternative, a transcriptionist may simply be notified that the electronic clinical document has new audio that is ready to be transcribed and be provided limited access to the electronic clinical document on the system. In embodiments of the present invention, the embedded dictation audio input is the only portion of the document that the transcriptionist is permitted to access.

As indicated at block 304, the electronic clinical document is presented to the transcriptionist using a graphical user interface that "locks" the underlying data in the document with respect only to the transcriptionist. In other words, the transcriptionist is allowed to view the data in the document, but cannot edit any of the existing data (i.e., the transcriptionist is not given "write access" to any of the existing data). This ensures the integrity of the document, as created by the user. Thus, the transcriptionist is given "read-only" access to the existing data, but is allowed to enter transcribed text associated with the embedded dictation audio input into the electronic clinical document. In an embodiment of the present invention, the underlying data in the electronic clinical document can be anonymized, such that actual patient identification information is replaced with alternate "John Doe" information to preserve medical confidentiality and patient anonymity.

The transcriptionist can view the graphical representation of the embedded dictation audio indicating the location or section where the dictation audio was input into the document. This allows the transcriptionist to see the context within which the dictation was recorded. For example, the transcriptionist can view other relevant information in the note to assist in transcribing the audio file. Also, the clinician or other user who populated the electronic clinical document can still access the document, including the dictation audio, even after a link or other reference has been sent to the transcriptionist. This feature allows the clinician to access the patient's complete electronic clinical document should the clinician have a need for the information before the transcriptionist has transcribed any embedded audio.

Subsequently, as indicated at block 306, a request is received to output the dictation audio. For example, the transcriptionist may double-click on the graphical representation of the embedded dictation audio input to initiate playback of the audio file. Then, as indicated at block 308, the stored dictation audio input is accessed and output. The audio file may be output via any audio output means, such as those described above with reference to FIG. 1. For instance, computer speakers or headphones may be used to output the audio.

Subsequently, as indicated at block 310, transcribed text associated with the dictation audio input is received and stored in association with the electronic clinical document. The transcription input can be received in a transcription entry box, such as that described below. After the transcriptionist indicates that the entry is complete, such as by selecting a "done" or "save" selectable indicator, the transcribed text is stored in the same location as the corresponding dictation audio input. For example, if the clinician embedded dictation audio input into a "physical examination" section of the electronic clinical document, then the transcribed text received corresponding to this dictation audio input is received into the "physical examination" section of the document. In this embodiment, the embedded dictation audio input is preserved to allow the clinician to listen to the recorded dictation audio again, for example, if the clinician notices any potential errors in the transcribed text. In this embodiment, the clinician may optionally edit the transcribed text as free text in order to make any corrections or additions.

In another embodiment, the dictation audio input may be automatically converted to transcribed text using voice recognition software. Various voice recognition techniques are known in the art and any can be used in conjunction with the present invention to allow real-time voice-to-text conversion. In the alternative, after a dictation audio file has been recorded and embedded, a voice-to-text conversion can be performed on the completed file to convert it to text. Similar to the manual transcription process discussed above, the embedded dictation audio input and graphical representation are preserved to allow the user to double-check the voice-to-text conversion.

Figure 4:
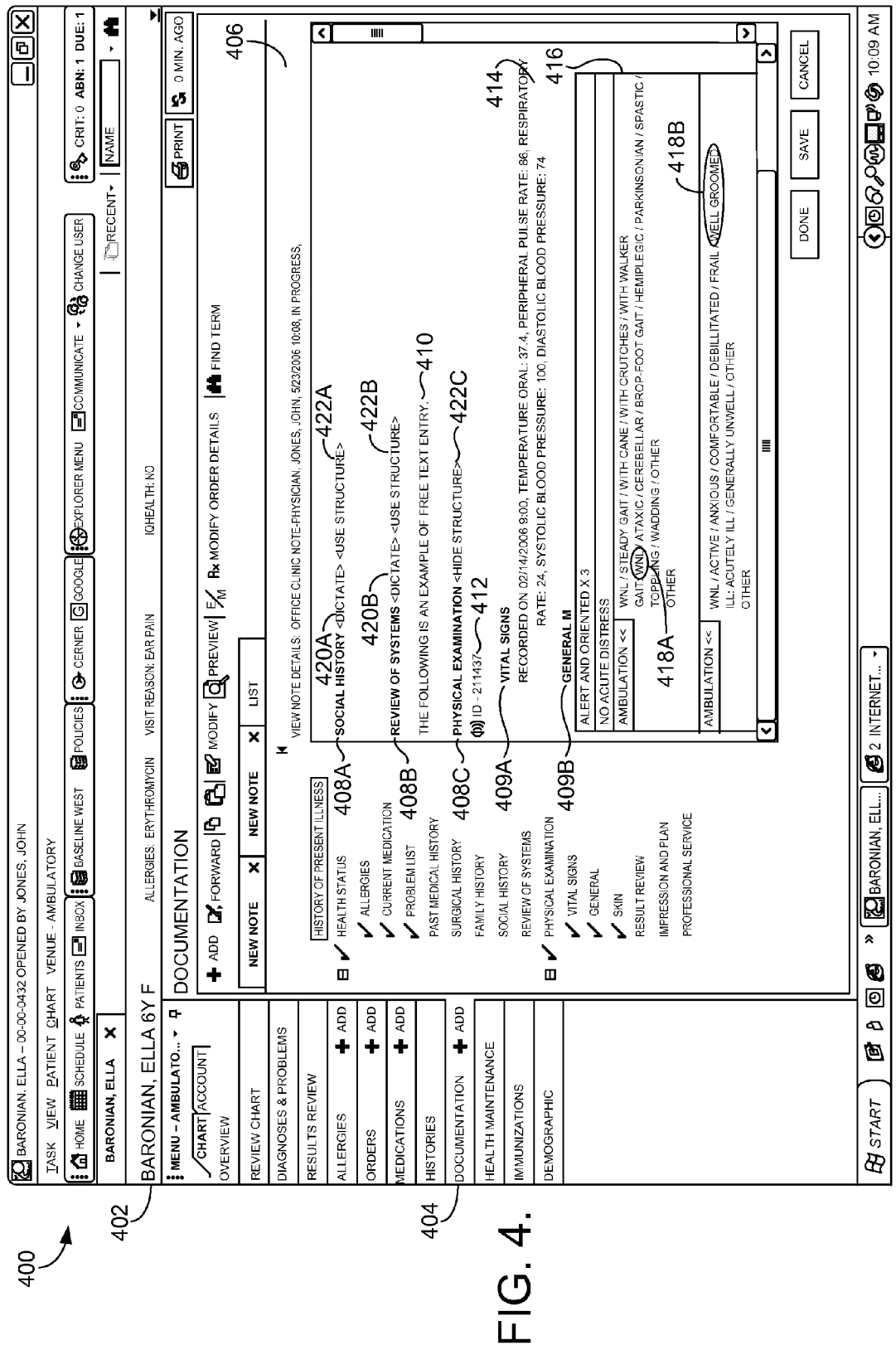
FIG. 4 is an exemplary screen display showing an electronic clinical document interface for receiving and presenting multiple types of data input, in accordance with an embodiment of the present invention.

Exemplary user interfaces for performing various embodiments of the present invention will now be discussed. These user interfaces are exemplary in nature and should not be treated as limiting. With reference to FIG. 4, an exemplary user interface 400 is provided for populating an electronic clinical document 406 with multiple types of data entry, including dictation audio input. An electronic clinical document can be a stand-alone electronic medical document or it can be part of an electronic clinical record stored within an electronic medical records system. In FIG. 4, for example, the electronic clinical document 406 is a part of an electronic clinical record 402 for a particular patient. In this case, an electronic clinical document is displayed for Ella Baronian, a 6-year old, female patient. The documentation portion of the electronic clinical chart 402 can be displayed using the documentation tab 404. The electronic clinical document 406 in this example is an office clinic note regarding Ella Baronian that is being populated by physician John Jones on May 23, 2006 at 10:08 A.M.

In embodiments of the present invention, the electronic clinical document 406 comprises a plurality of sections 408A-C. The plurality of sections can be displayed on a common user interface, such as within a single tab (e.g., documentation tab 404) or on a single-screen view. If the electronic clinical document contains more information than can fit in the allotted screen area of a display device, then a scroll bar or other navigation buttons can be used to allow the user to navigate to additional information within the tab. In embodiments, the sections 408A-C can further comprise subsections, such as subsections 409A-B. These sections (and subsections) categorize clinical information relevant to the treatment of a particular patient. By way of example, and not limitation, these sections and subsections can include categories such as history of present illness, health status, allergies, current medications, problem lists, past medical history, surgical history, family history, social history, review of systems, physical examination, vital signs, general information, skin conditions, laboratory and test results, physician impression and plan, professional service, etc. Each of these sections (and subsections) may be capable of receiving multiple types of data entry, including dictation audio input, structured user input, free-text input, and system generated input. In addition, in an embodiment, multiple instances of each data type may appear within one or more of these sections. Further, the subsections can be alternatively displayed or hidden using substructure display regions, such as substructure display regions 422A-C. When any of the substructure display regions 422A-C is selected, subsections are displayed if not currently displayed and hidden if currently displayed. In this example, subsections 409A-B are revealed, but can be hidden by a user selecting substructure display region 422C, which is labeled "hide structure." Each of these subsections can receive dictation audio input, structured user input, free-text input, and system-generated input, in any combination or in any number of instances.

Further, in this embodiment, each of the electronic clinical document sections 408A-B has a corresponding dictation selection region 420A-B operative to receive requests to receive dictation audio input. In embodiments, when dictation audio input is received, it is recorded and embedded directly into the electronic clinical document 406 and represented by a graphical representation 412, such as an icon, indicative of the embedded dictation audio input associated with the particular section. In this example, dictation audio input has been embedded into section 408C, labeled as "physical examination" and is represented by graphical representation 412. In this embodiment, the graphical representation 412 includes an associated dictation identifier that identifies the section, electronic clinical document, and the patient. In this case, the ID number "211437" associates the embedded dictation audio with the "physical examination" section, with this particular office clinic note created by Dr. John Jones on May 23, 2006, and with patient Ella Baronian.

In this example, user interface 400 also displays free-text input 410 that has been input into section 408B of electronic clinical document 406. As described above, any alpha-numeric text or other text typically used by common word-processing applications can be entered as free-text input. In an embodiment, graphics may be embedded in the same manner that graphics are commonly embedded into word processing documents by conventional word processing applications. Though FIG. 4 displays free-text only in one section of the electronic clinical document, any of the sections can receive free-text input, including multiple instances of free-text input within an individual section.

In this example, the electronic clinical document 406 also displays structured user input 416 that has been entered into subsection 409B. In this case, the general subsection of the physical examination section has received structured user input in an ambulation form with structured user input selections 418A-B. Structured user input selection 418A indicates that the patient's gait was "WNL" or within normal limits, and structured user input selection 418B indicates that the patient was "well groomed." Though electronic clinical document 406 displays structured user input within only one section, each section can contain structured user input, including multiple instances of it within individual sections. Further, structured user input 416 is merely exemplary in nature and should not be considered limiting. As described above with reference to FIG. 3, structured user input can be entered by way of any pre-defined template, form, table, etc. having various pre-defined selection options.

Further, the electronic clinical document 406 also displays system-generated input 414. System-generated input includes both auto-populated input and user-driven-populated input, as described in more detail above with reference to FIG. 2. In this example, the electronic clinical document 406 has received system-generated input 414 through auto-population. In this embodiment, the patient Ella Baronian's vital signs from a recent patient visit have been auto-populated into Dr. Jones' office clinic note. In this case, the system-generated input received includes the patient's oral temperature, peripheral pulse rate, respiratory rate, systolic blood pressure, and diastolic blood pressure. In another embodiment, the user may indicate that he or she wishes to populate an electronic clinical document with laboratory test results, such as by using a pull-down window. In this instance, laboratory test results stored elsewhere in the system are populated into a desired section of the electronic clinical document via user-driven population. Any type of information relevant to the patient stored elsewhere within the patient's record or elsewhere on the system can be populated as system-generated input into the electronic clinical document. By using system-generated input (in either form), a user can conveniently avoid having to re-enter data that is already available elsewhere in the system, saving time and avoiding clerical mistakes.

FIGS. 5-9 provide exemplary screen displays of a sequence of screens that can be used to receive dictation audio input and subsequent corresponding transcribed text associated therewith into an electronic clinical document.

Figure 5:
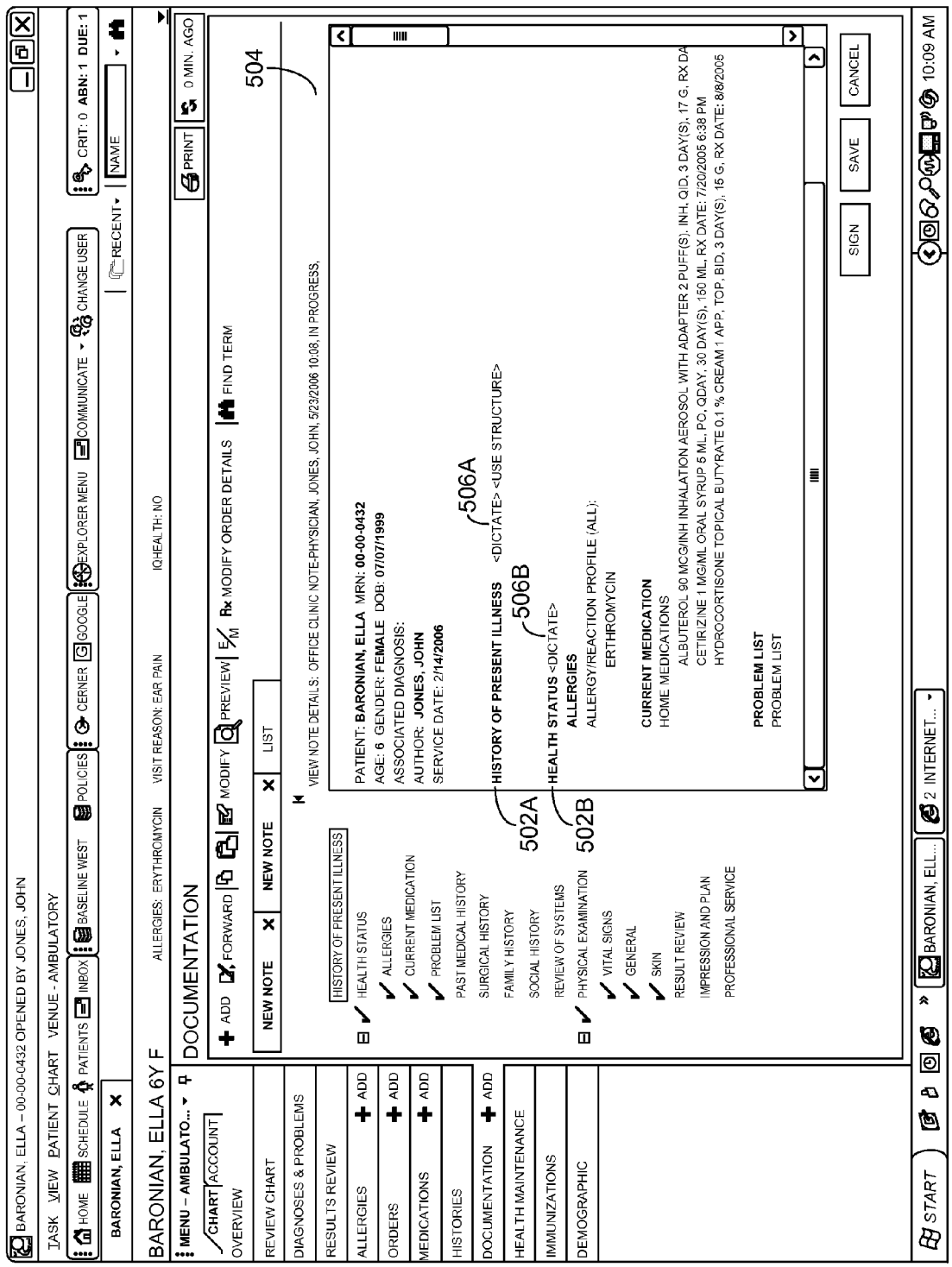
FIG. 5 is an exemplary screen display of an electronic clinical document for receiving and embedding dictation audio input, in accordance with an embodiment of the present invention.
Figure 6:
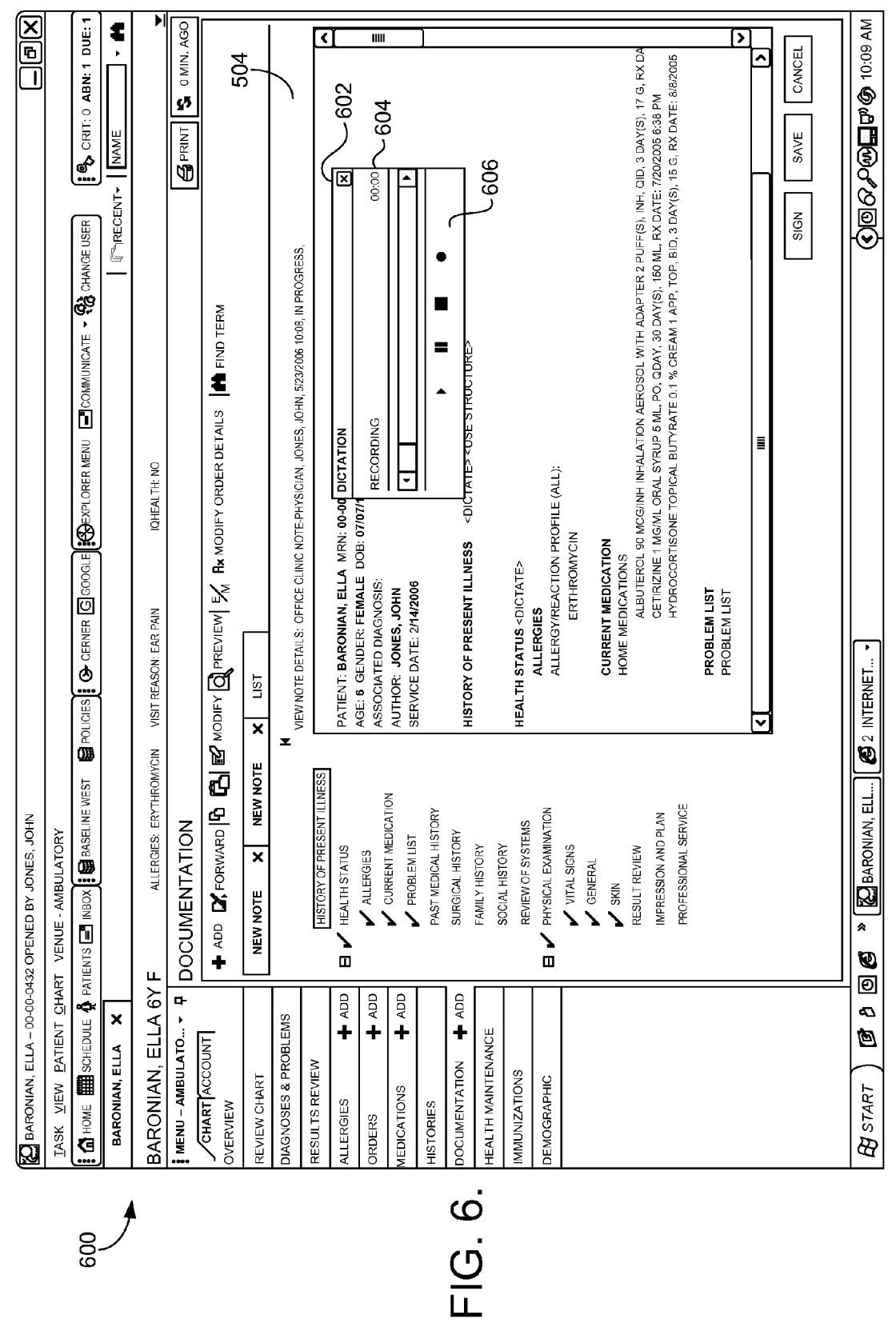
Figure 7:
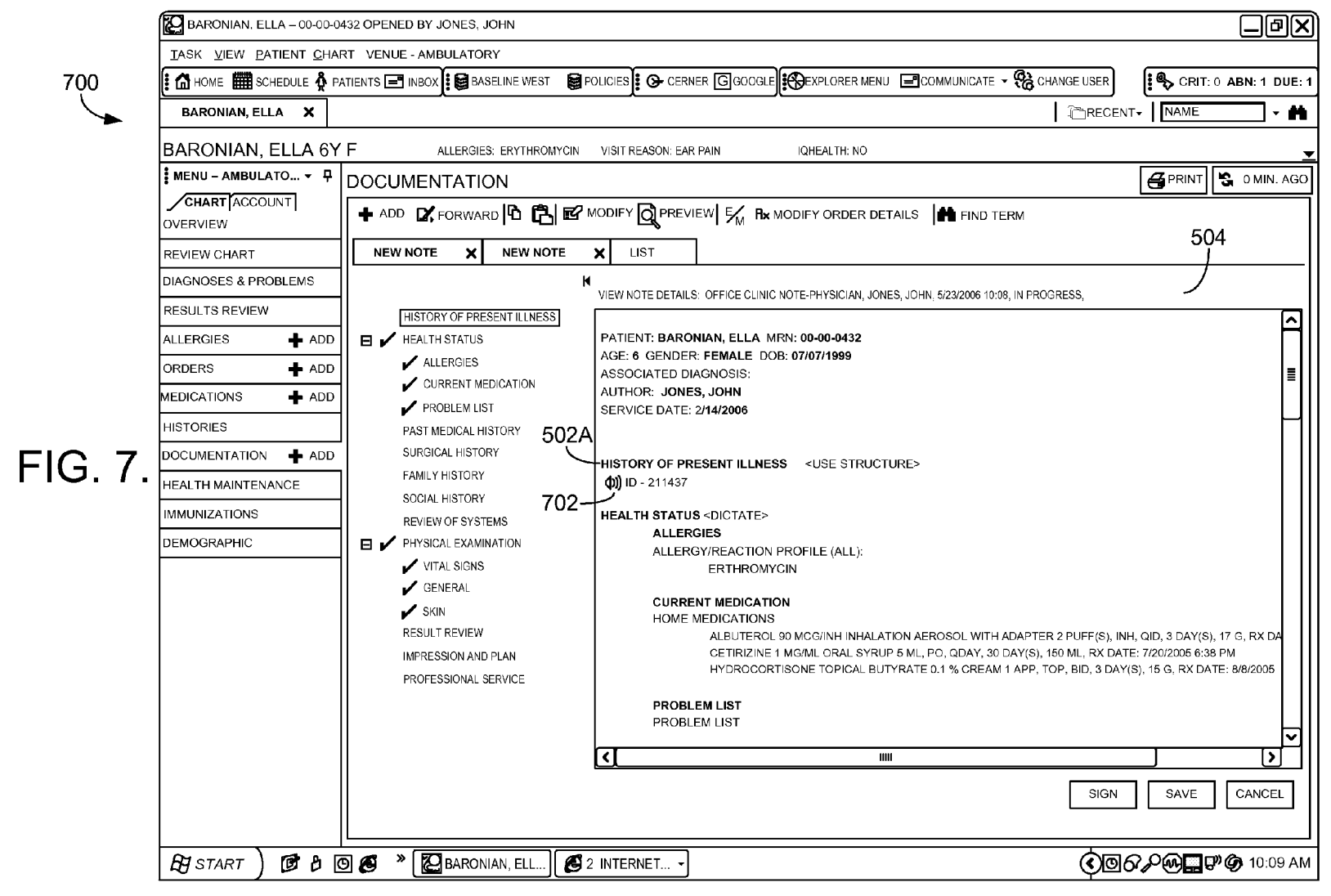

With reference to FIG. 5, an exemplary screen display 500 is shown which presents an electronic clinical document 504. The electronic clinical document 504 comprises a plurality of sections 502A-B. Within sections 502A-B are corresponding dictation selection regions 506A-B, which are capable of receiving requests to receive dictation audio input to be embedded into the respective sections. Upon selection of dictation selection region 506A within section 502A, labeled as "history of present illness," a user interface 600 is displayed for receiving dictation audio input, as shown in FIG. 6. User interface 600 displays a dictation pop-up window 602 operative to receive dictation audio input. Dictation pop-up window 602 comprises a recording status display 604 and recording controls 606. This user interface is merely exemplary in nature and should not be deemed limiting. The dictation pop-up window 602 allows a user to start recording dictation audio input, pause recording, re-play recorded dictation audio, and stop recording. Once the user selects to stop recording, the received dictation audio input is embedded into the electronic clinical document 504 and represented by a graphical representation 702, as shown by exemplary user interface 700 in FIG. 7. Graphical representation 702 appears in the same section 502A in which the dictation selection region 506A was selected. In this instance, graphical representation 702 is an icon indicating that dictation audio input has been received and embedded into the "history of present illness" section (section 502A) of electronic clinical document 504. This embodiment is merely exemplary in nature and should not be deemed limiting.

Figure 8:
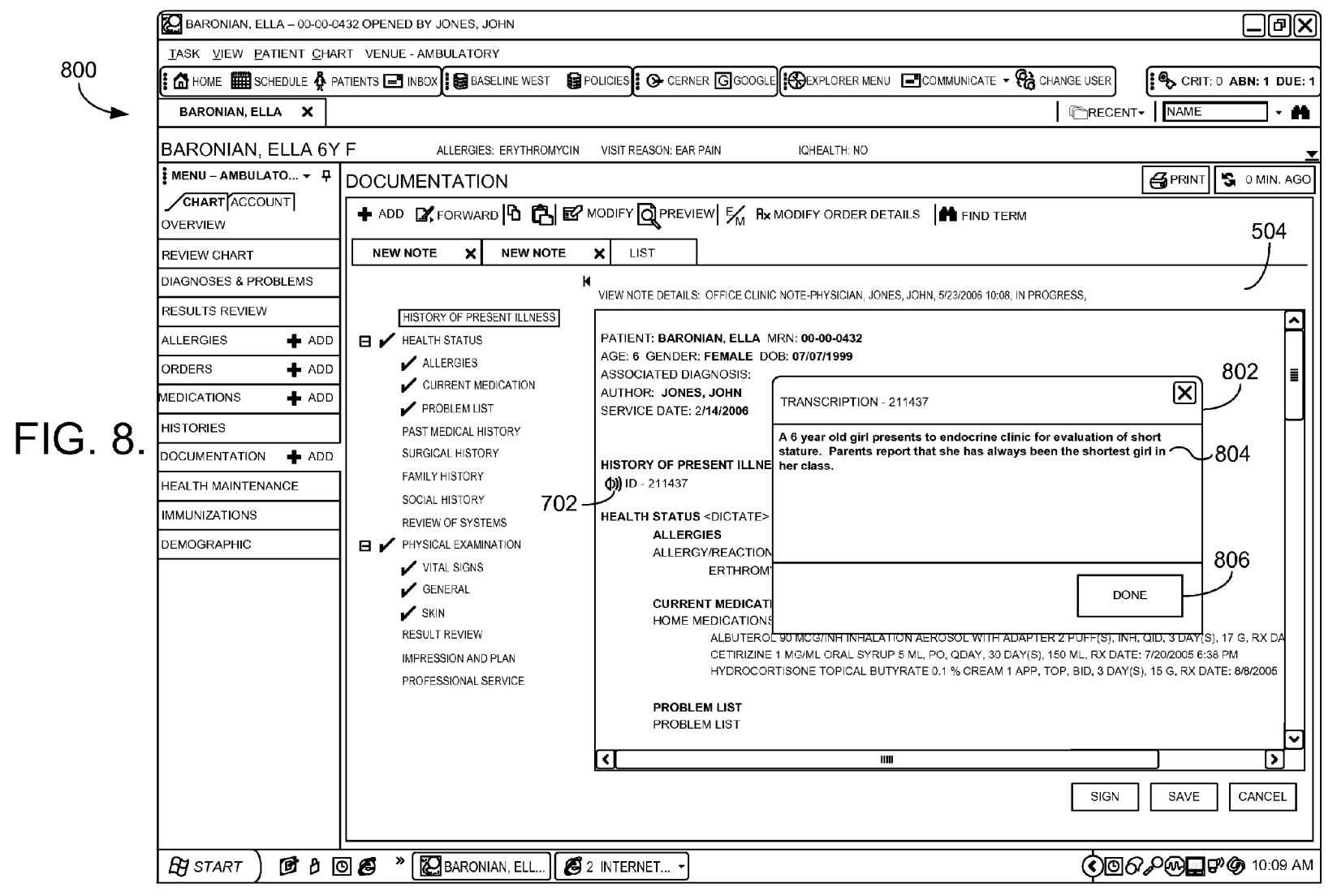
Figure 9:
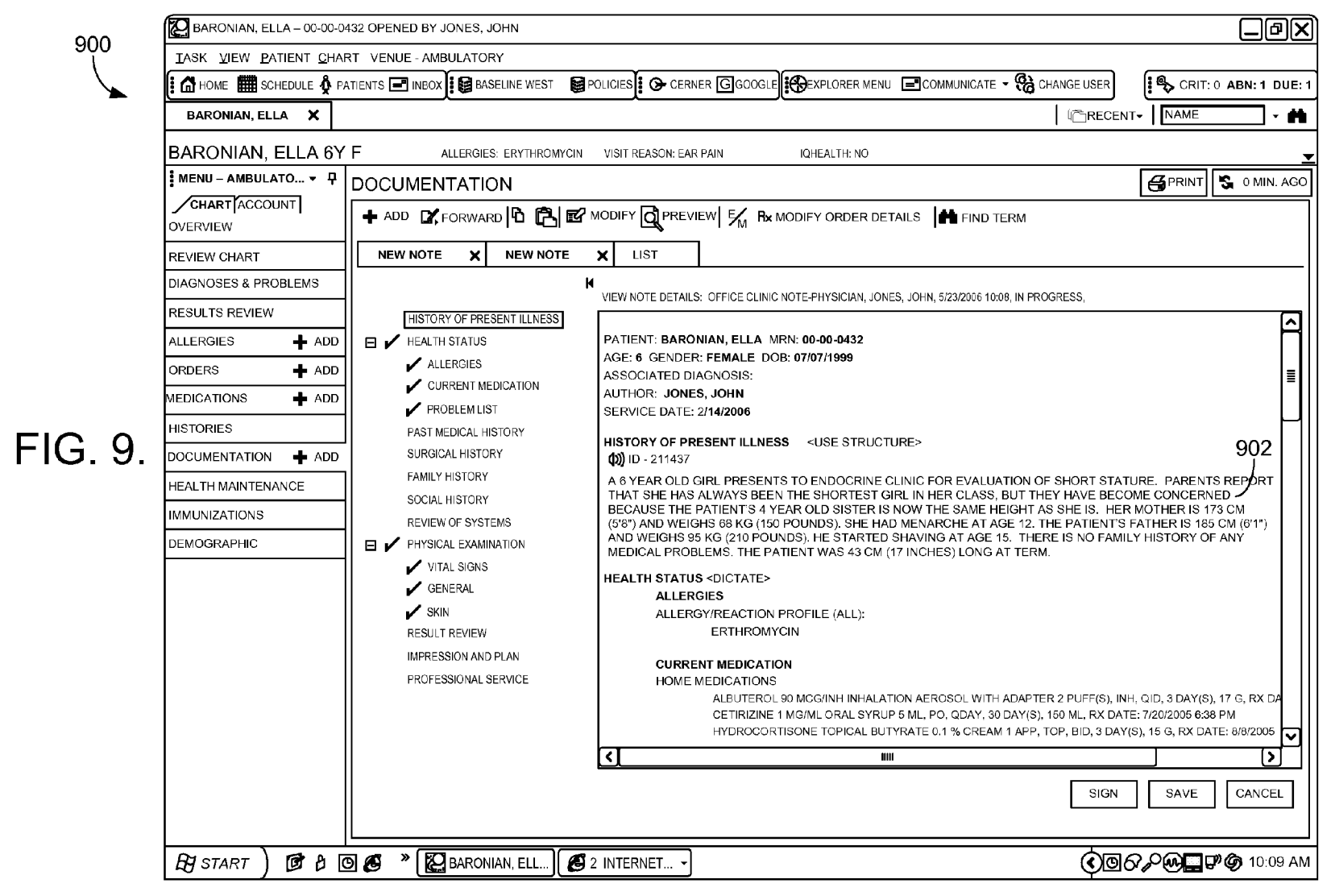

With reference to FIG. 8, an exemplary screen display 800 is shown for receiving transcribed text from a transcriptionist based on embedded dictation audio input received into the electronic clinical document 504. After a user has input dictation audio into an electronic clinical document, it can be transmitted to a transcriptionist, as described above. It can be transmitted separately or it can be transmitted as part of the electronic clinical document, with the underlying layers of the document "locked", as described above. In this embodiment, display 800 shows the latter, with the embedded dictation audio in the context of the underlying "locked" layers of the electronic clinical document 504. Upon selection of the graphical representation 702, the associated dictation audio is output via any of the audio output means discussed above. Also, in this embodiment, a transcribed text input window 802 is displayed for receiving transcribed text 804 from the transcriptionist. Once the transcription is complete, the transcriptionist can select region 806 to indicate completion. Upon selection of region 806, the transcribed text is placed into the corresponding section where the associated dictation audio input is embedded. FIG. 9 displays an exemplary screen 900 showing this text input as transcribed text 902 within the corresponding section where the associated dictation audio input is embedded.

With reference to FIG. 10, in another embodiment, an exemplary screen display 1000 can be used to receive transcribed text from a transcriptionist based on embedded dictation audio input. In this embodiment, the transcribed text is received into a window 1002. A preview window 1004 displays a preview of the preliminary report corresponding to an electronic clinical document.

Figure 11:
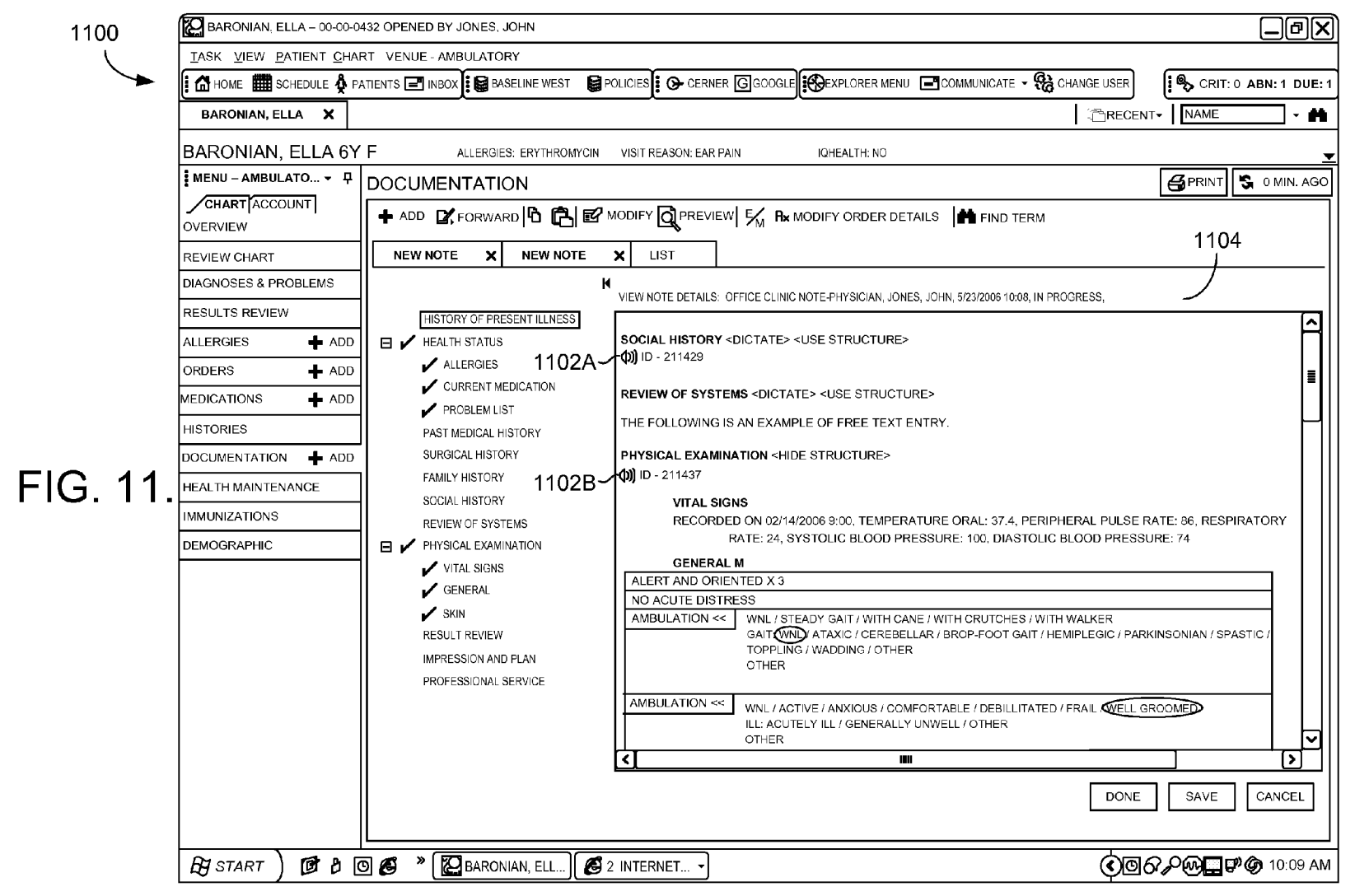

With reference to FIG. 11, an exemplary screen display 1100 is shown which displays graphical representations 1102A-B corresponding to separate dictation audio inputs that have been embedded into multiple sections of an electronic clinical document 1104. In accordance with embodiments of the present invention, multiple sections of electronic clinical documents can receive embedded dictation audio input, as well as the other types of input discussed above.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated by and within the scope of the claims.

The invention claimed is:

1. A method in a computerized healthcare system for populating an electronic clinical document, the method comprising:
providing an electronic clinical document for a particular patient, the electronic clinical document being capable of receiving dictation audio input, structured user input, free-text input, and system-generated input;
receiving dictation audio input into the electronic clinical document, wherein the dictation audio input is audio data;
receiving at least one of structured user input, free-text input, and system-generated input into the electronic clinical document;
embedding the dictation audio input directly into the electronic clinical document;
presenting graphical representations indicative of the embedded dictation audio input in the electronic clinical document; and
assigning a dictation audio identifier to each of the graphical representations, wherein the dictation audio identifier associates the dictation audio input with the particular patient, the electronic clinical document, and a location of the dictation audio input within the electronic clinical document.

2. The method of claim 1, wherein the electronic clinical document comprises a plurality of sections.

3. The method of claim 2, wherein the dictation audio input and the at least one of structured user input, free-text input, and system-generated input are received into one of the plurality of sections of the electronic clinical document.

4. The method of claim 2, wherein the plurality of sections are displayed in a common user interface.

5. The method of claim 2, wherein the plurality of sections are displayed within a single tab.

6. The method of claim 2, wherein the plurality of sections are displayed within a single-screen view.

7. The method of claim 1, wherein the dictation audio input is received into at least two of the plurality of sections of the electronic clinical document.

8. The method of claim 1, further comprising receiving a transcribed body of text associated with the dictation audio input.

9. The method of claim 8, further comprising receiving additional dictation audio input into the transcribed body of text.

10. One or more computer storage media having computer executable instructions embodied thereon for performing a method in a computerized healthcare system for populating an electronic clinical document having a plurality of sections, the method comprising:
providing an electronic clinical document for a particular patient having a plurality of sections, at least one of the plurality of sections being capable of receiving input of multiple data types;
receiving dictation audio input into at least two of the plurality of sections, wherein the dictation audio input is audio data;
embedding the dictation audio input directly into each of the at least two of the plurality of sections;
presenting graphical representations indicative of the embedded dictation audio input in association with each of the at least two of the plurality of sections; and
utilizing a dictation audio identifier to associate the dictation audio input with the particular patient, the electronic clinical document, and a location of the dictation audio input within the electronic clinical document.

11. The computer storage media of claim 10, wherein the at least one of the plurality of sections that is capable of receiving input of multiple data types is capable of receiving at least dictation audio input, structured user input, free-text input, and system-generated input.

12. The computer storage media of claim 10, wherein the method further comprises receiving at least one of structured user input, free-text input, and system-generated input into one of the at least two sections having dictation audio input embedded therein.

13. The computer storage media of claim 12, wherein the method further comprises presenting the at least one of structured user input, free-text input, or system-generated input in association with the section into which it was received.

14. The computer storage media of claim 10, wherein the method further comprises receiving into one or more of the at least two of the plurality of sections, transcribed text associated with the dictation audio input embedded therein.

15. The computer storage media of claim 14, wherein the method further comprises:
presenting the transcribed text within the at least one of the plurality of sections with which the dictation audio input associated with the transcribed text is embedded.

16. The computer storage media of claim 10, wherein the plurality of sections are provided in a common user interface.

17. The computer storage media of claim 10, wherein the plurality of sections are provided in a single-screen view.

18. The computer storage media of claim 10, wherein the plurality of sections are provided within a single tab.

19. One or more computer storage media having computer executable instructions embodied thereon for performing a method in a computerized healthcare system for populating an electronic clinical document having a plurality of sections, the method comprising:

providing an electronic clinical document for a particular patient, the electronic clinical document having a plurality of sections, wherein at least one of the sections is capable of receiving dictation audio input, structured user input, free-text input, and system-generated input, and wherein the plurality of sections are displayed within a single-screen view;

receiving the dictation audio input into the electronic clinical document, wherein the dictation audio input is audio data, and wherein while the dictation audio input is being received into the electronic clinical document, existing data in the electronic clinical document is locked so that read-only access is given to the existing data;

receiving the free-text input into the electronic clinical document;

embedding the dictation audio input directly into each of the at least two of the plurality of sections;

presenting graphical representations indicative of the embedded dictation audio input in association with each of the at least two of the plurality of sections;

providing a dictation audio identifier for each of the graphical representations; and utilizing the dictation audio identifier to associate the dictation audio input with the particular patient, the electronic clinical document, and a location of the dictation audio input within the electronic clinical document.

* * * * *